United States Patent
Storz

(10) Patent No.: US 6,513,524 B1
(45) Date of Patent: Feb. 4, 2003

(54) INHALER FOR PRODUCTION OF AROMA- AND/OR ACTIVE SUBSTANCE-CONTAINING VAPORS OF PLANT MATERIALS AND/OR FLUIDS

(76) Inventor: Markus H. Storz, Gauss-Strasse 6, 78532 Tuttlingen (DE)

(*) Notice: Subject to any disclaimer, the term of this patent is extended or adjusted under 35 U.S.C. 154(b) by 0 days.

(21) Appl. No.: 09/238,545

(22) Filed: Jan. 28, 1999

(30) Foreign Application Priority Data

Jan. 29, 1998 (DE) .......................................... 198 03 376

(51) Int. Cl.$^7$ .............................................. A61M 16/00
(52) U.S. Cl. ........................... 128/203.26; 128/203.27; 128/203.28; 128/203.29
(58) Field of Search ...................... 128/203.17, 203.26, 128/203.27, 203.29, 203.28, 203.12, 202.21; 131/329, 202, 214, 215.1, 215.2, 215.3

(56) References Cited

U.S. PATENT DOCUMENTS

| | | | | |
|---|---|---|---|---|
| 649,521 A | * | 5/1900 | Libbey | 128/203.22 |
| 1,357,601 A | * | 11/1920 | Walter | |
| 3,115,134 A | * | 12/1963 | Schmahl | 128/203.27 |
| 3,949,743 A | * | 4/1976 | Shanbrom | 128/173.1 |
| 4,083,374 A | * | 4/1978 | Jacobsen | 131/178 |
| 4,807,646 A | * | 2/1989 | Sahar | 131/175 |
| 4,922,931 A | * | 5/1990 | Nare et al. | 131/211 |
| 4,967,742 A | * | 11/1990 | Theodorou | 128/202.13 |
| 5,086,766 A | * | 2/1992 | Beacham | 128/203.27 |
| 5,558,084 A | * | 9/1996 | Daniell et al. | 128/203.17 |
| 5,598,835 A | * | 2/1997 | von Schrader | 128/200.21 |
| 5,613,489 A | * | 3/1997 | Miller et al. | 128/200.14 |
| 6,250,301 B1 | * | 6/2001 | Pate | 128/202.21 |

FOREIGN PATENT DOCUMENTS

| | | | | |
|---|---|---|---|---|
| DE | 195 41 690 A1 | 10/1996 | .......... | A61M/15/00 |
| DE | 195 41 528 A1 | 5/1997 | .......... | A61M/15/00 |
| DE | 296 10 936 U1 | 7/1997 | .......... | A61M/15/00 |

* cited by examiner

Primary Examiner—Dennis Ruhl
Assistant Examiner—Mital Patel
(74) Attorney, Agent, or Firm—Pendorf & Cutliff

(57) ABSTRACT

Process for inhalation and inhaler for production of aroma- and active-substance containing vapors of plant material and/or fluids via hot air.

The previous apparatuses conceived for this—in comparison to smoking—hazardous-substance-free vaporizing of active substances of plant material were too inconvenient in their operation, so that they were not successful. The new inhaler makes it possible to flow the hot air through the portion of plant material to be vaporized or the fluid with one pass, and yet to make it possible that inhalation can occur independently and comfortably in multiple inhalations.

Herein the produced vapors are collected in a balloon and thereafter inhaled using a valve mechanism with associated mouthpiece independently of the vapor generator.

The inhaler makes it possible, to inhale the active substances of the therefore suitable plant material (such as, for example, tobacco), without exposing the user to the hazardous substances which would occur during combustion. Further, one can, for example, for aroma therapy, vaporize the appropriate plants or fluids (such as for example volatile or essential oils) and selectively inhale or blow the vapors into the ambient atmosphere.

12 Claims, 2 Drawing Sheets

INHALER FOR PRODUCTION OF AROMA- AND/OR ACTIVE SUBSTANCE-CONTAINING VAPORS OF PLANT MATERIALS AND/OR FLUIDS

BACKGROUND OF THE INVENTION

1. Field of the Invention

At the present time aroma- and active substance-vapors for aroma therapy are primarily produced by three processes, namely 1. by inhalers in which aroma- and active substance-containing fluids together with a suitable solvent are atomized to an aerosol mixture which can then be inhaled.
2. by vaporizers in which aroma- and active substance-containing fluids likewise dissolved in an appropriate solvent are brought into the ambient atmosphere by vaporizing.
3. by burning or, as the case may be, smoldering of suitable plants or products thereof (mostly resins). Herein the smoke produced by burning is emitted into the ambient atmosphere (as with incense or incense sticks) or inhaled by means of cigarettes (special asthma cigarettes with therapeutic herbs are available for acute attacks for asthmatics).

All three processes are associated with disadvantages. For example, in order to produce aroma- and active substance-containing fluids, plants must first be extracted in a complicated manner. The solvent, in which the fluids are then dissolved, are in certain cases not suitable for certain persons (for example allergy sufferers). In the case of incense fragrances or smoking of plant materials (this obviously includes tobacco) hazardous side products of combustion are produced such as, for example tar, nitrosamine or even soot containing solids, which are contra-indicated to therapeutic applications.

2. Description of the Related Art

In the design application (Roll Number DE 296 10 936 U1) of Jun. 21, 1996, there is described a device for production of aroma- and active substance-vapors using hot air. This concerns a hot air generator which cannot satisfy its purpose without suitable auxiliary means (pipe).

This inhaler is very impractical in operation. So, for example, for each inhalation the hot air generator must be turned on and off again, whereby one must precisely time the right instant for inhalation. If one inhales too early, then one inhales hot air free of active substance (the active substances become entrained in the hot air only after several seconds), if one inhales too late, then a part of the active substance containing vapor is ineffectively vented into the ambient atmosphere. Besides this, one must match his inhalation to the conveyance capacity of the hot air blower, which can lead to choking and substantial coughing attacks. The temperature of the vapor which is still high represents a further problem.

From DE 195 41 528 A1 as well as from DE 195 41 690 A1 inhalers are known which include a reservoir for collection of produced aroma- and/or active substance-containing vapors, which is removably connected with the rest of the inhaler. The reservoir can be removed for purposes of cleaning. During the inhalation process the reservoir must be operated together with the rest of the inhaler as a unit. Thereby the described inhalers have proven themselves to be very inconvenient, which makes utilization very difficult particularly in the case of employment with bed-ridden or handicapped patients.

SUMMARY OF THE INVENTION

The present invention is concerned with the task of improving an inhaler in such a manner that the above discussed disadvantages are overcome to the greatest extent possible and in particular it is made suitable for the employment with bed-ridden or handicapped patients.

The invention is based essentially on the idea that, first, hot air is blown through the plant material and thereby the aroma- and active substances are transitioned into vapor, wherein however the entire "portion" is vaporized in one draw and is directed into a balloon via a valve and is collected there. The vapor can then be inhaled out of this balloon by means of a mouthpiece connected to the valve.

The advantages provided by the invention are comprised particularly therein, that the material to be vaporized can be aspirated with hot air in one draft without interruption or settlement. Further, the vapors collected and cooled in the balloon can then be very comfortably inhaled independently of the table-top apparatus. With this means and manner it becomes possible, for example, for the care-givers to fill a balloon which can then simply be handed over to a bed-ridden patient.

A further development of the invention makes it possible to introduce a crucible into the receptacle, from which essential or volatile oils or other fluids can then be vaporized.

A second further development of the invention makes it possible, to draw the produced vapor/air mixture out of the balloon by means of a compressor for compressing and filling into a pressure container, or to directly fill the produced vapors via a compressor into a pressure container.

This has the advantage that one can, at home, fill an appropriate portion into a container which is small and convenient to transport, and carry this with him for use when needed.

A third further development of the invention makes it possible to avoid burning the herbs in the case that the temperature is set too high.

It is known that, for example in an electronically controlled hot air hair dryer, a temperature sensor continuously compares the actual value with the desired value and via the electronic control insures that the temperature always corresponds to a set level.

In accordance therewith a smoke detector is incorporated into the receptacle above the receptacle chamber, which monitors the ascending vapor/air mixture and upon the development of undesired smoke, which is brought about by the beginning of the burning of the herb, gives a signal to the controller, which thereby immediately reduces the temperature in order to prevent a further smoldering or, as the case may be, combustion of the herb.

BRIEF DESCRIPTION OF THE DRAWINGS

A working example of the invention is described in the following in greater detail by reference to the drawings. There are shown.

DETAILED DESCRIPTION OF THE INVENTION

Figure 1:
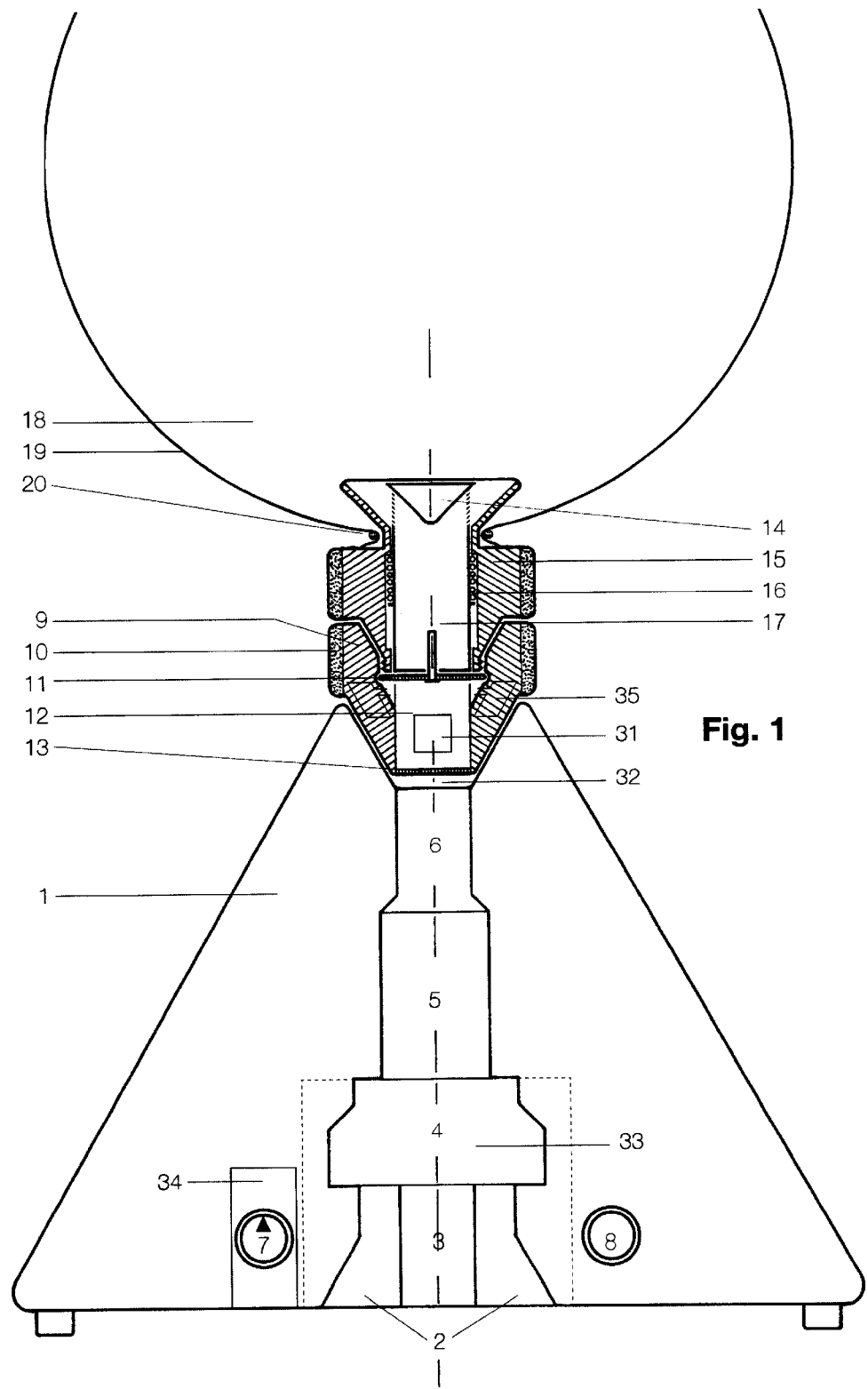
FIG. 1: an inhaler according to the invention with seated receptacle and valve as well as vapor balloon.

FIG. 1 shows the table-top apparatus with seated receptacle 9 and valve 15 as well as the vapor balloon 18. The housing 1 is preferably designed "volcano"-cone shaped, which is advantageous for the stance or standing stability of the apparatus. Further, the crater shape of the "volcano" insures therefore, that the seated receptacle 9 is guided by itself without fumbling to its correct position. The same applies for the valve 15 to be seated in the receptacle 9. In the inside of the housing 1 there is a (schematically represented) hot air generator comprised of a motor 3, propeller 4, heat chamber 5 and air flow tube 6 which draws in the air from below through an air inlet provided in the base, heats and, following the laws of physics, in accordance with which heated air climbs upwards, conveys this upwards ("volcano"—smoke stack).

In principle it is not important in which means and manner the necessary hot air is produced, it is conceivable for example to incorporate an incandescent light in the heat chamber, which then has the advantage, that one can better recognize the vapors as a result of the upwardly emitted light. It must however be achieved, that the hot air generator is in condition, to bring the air into the temperature of between 50° and 300° C. Obviously no hazardous emissions can be produced by the means and manner of the hot air production which will be contrary to the medical use of the device. Further there is situated on the outside of the housing 1 a temperature regulator 7 as well as an on/off switch 8, which must be constructed as a push button, so that the hot air generator works only upon pushing down of the push button. The receptacle 9, preferably produced of a light metal, includes a receptacle chamber 12 in which either the plant material to be vaporized is loosely filled in or the crucible 13 with the fluid to be vaporized is introduced. This crucible is stream-line shaped (such as a container with the tip towards below, upwardly open) formed with only approximately half so large a diameter as the receptacle chamber and precisely centered in the middle of the receptacle chamber by three or four outwardly directed spacers, so that it is surrounded by hot air and the therein situated fluid can be heated and vaporized. Below the receptacle 9 there is situated a screen 13 rigidly connected with the receptacle, which prevents the falling downward of filled material, however allows the hot air to flow through without impedance. A sieve 11 encloses the upper end of the receptacle, in order to prevent that plant material is blown towards upwards into the valve 15. This sieve is removable in order to make possible the filling and emptying of the filled chamber.

In order to simplify the removal of the sieve, a tab is provided projecting upwardly from the middle of the sieve. The receptacle further comprises a smoke detector 35 to monitor the vapor upon the development of undesired smoke. The smoke detector provides a signal to a controller 34 to regulate the temperature of the hot air source. Further the receptacle as well as the valve piece are on the outside surrounded by a broad rubber ring 10, which provides a good grip as well as isolation from the heated metal. The receptacle is removable for the simplified filling and cleaning in the same way as the valve, and is held in the correct place only by its conical shape and by gravity. The valve 15 is comprised of a light metal block in which a valve cylinder 17 and a valve spring 16 wound on the outside of the valve cylinder are provided.

FIG. 1 shows the valve in the opened condition. When the valve spring 16 is detensioned, the valve is closed. The valve cylinder 17 is rigidly connected with the valve cover 14 via spacers. The openings between the spacers make it possible for the vapor to can travel into and out of the balloon while the valve is opened. The funnel-like design of the exhaust opening of the valve piece 15 insures that during filling at first the limp balloon jacket 19 does not come in immediate contact with the hot vapor, of which the temperature is further reduced by the enlarged outlet surface area. Besides this the funnel shape itself protects, when the valve is open, the valve lid and the towards the cylinder extending thin spacers from possible damage, insures for a perfect sealing when the valve is closed, and also holds the balloon 18 securely in its place.

The vapor balloon 18 is comprised of the balloon jacket 19 and the balloon retainer 20. It should be offered in the most various sizes corresponding to the intended uses. The balloon jacket is comprised of a non-elastic, heat resistant plastic, which can be darkly colored for the protection of the possibly light-sensitive contents.

Figure 2:
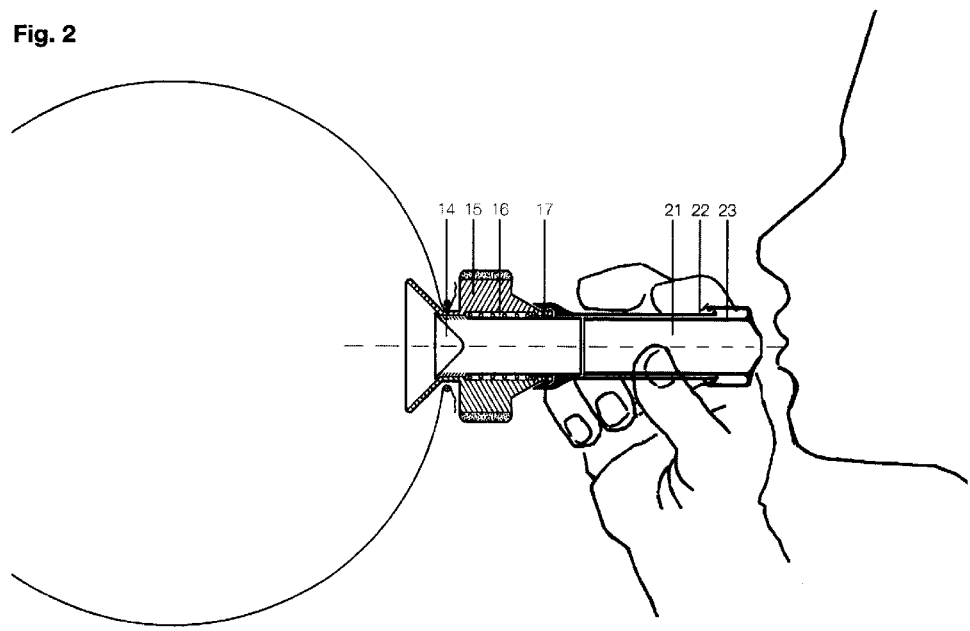
FIG. 2: the filled vapor balloon with closed valve and mouthpiece immediately prior to inhalation

FIG. 2 shows the filled balloon with valve (valve closed) with the mouthpiece 21 screwed on as well as a schematically represented person immediately prior to inhalation.

Figure 3:
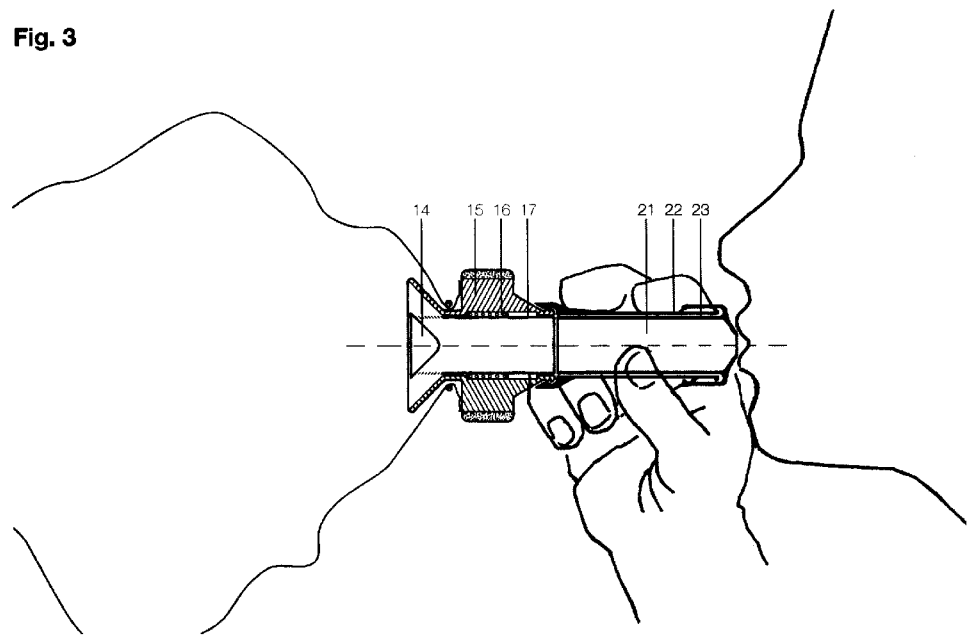
FIG. 3: the half filled vapor balloon with open valve and mouth piece during inhalation.

The mouthpiece 21 is preferably comprised of plastic and is preferably comprised of two pieces, namely, an outer cylinder 22 and an inner cylinder 23. The outer cylinder 22 is connected with the valve 15. This can be accomplished by screwing on, as shown, by a bayonet connection, or by a simple pushing in. The inner cylinder 23 exhibits a mouthpiece formed thereon, which can slide within the outer cylinder 22, exhibits the same diameter and the same amount of slide as the valve cylinder 17. The inner cylinder 23 is, as shown, secured against a falling out from the outer cylinder 22 by an overlapping. FIG. 3 shows how the valve can be opened by light pressure of the lips upon the mouthpiece, whereupon the path is opened for inhalation.

A compressor 33 is provided to draw the produced vapor/air mixture out of container and filling a pressure container.

1. First one takes the receptacle and fills the receptacle chamber with the shredded plant material or with the fluid-filled crucible. Then the upper sieve is again seated in place in order to prevent that the plant material is blown into the valve. Now one can seat the receptacle in the "volcano"-crater.
2. The necessary temperature is set at the regulator. This depends upon the moisture content and the type of the plant material. The damper the material, the higher the necessary temperature. Should the temperature be too low, then no vaporization occurs; if it is too high, then the plant material is caused to burn.
3. Now the on/off switch is operated. A few seconds pass before the air and the filled material have warmed up to the point that a vaporization occurs.
4. As soon as one sees vapor rising from the "volcano", then one seats the valve piece with the thereupon secured empty vapor balloon. The valve is thereby automatically opened and after a few seconds the balloon is filled and is again removed, whereby the valve automatically closes again, so that no vapor can escape. At the same time the finger is removed from the on/off switch, the apparatus is then switched off.
5. Now one need only screw the mouthpiece upon the valve and can then being with the inhalation.

By light pressure of the lips upon the mouthpiece the valve is opened and the balloon content can independently be inhaled time and again.

It is understood, that if one desires to release the vapors into the room air, that no balloon with valve is seated. Should as a result of inattention the hot air generator continue to run after the balloon is completely filled, so then the balloon together with the valve (supported by the force of the valve spring) is lifted by the air pressure and the overflow air can escape through the resulting gap between the valve and receptacle piece. There is thus no need for a supplemental safety mechanism.

Should it prove necessary to provide a mechanical filter for air, this can be provided in the following positions:

1. Integrated with the upper sieve 11.
2. In the valve cylinder. Herein a double filtering occurs; once during filling and once during emptying of the balloon.
3. In the inner cylinder 23 of the mouthpiece.

REFERENCE NUMBER LIST

1 housing, hot air generator
2 air inlet
3 motor
4 propeller
5 heat chamber
6 air flow tube
7 temperature regulator
8 on/off switch
9 receptacle
10 rubber ring
11 sieve
12 receptacle chamber
13 screen
14 valve lid
15 valve
16 valve spring
17 valve cylinder
18 vapor balloon, container
19 balloon jacket
20 balloon retainer rubber
21 mouthpiece
22 outer cylinder
23 inner cylinder

What is claimed is:

1. An inhaler for providing aroma and/or active substance containing vapors, comprising:
    a housing;
    a receptacle seated on the housing and having a receptacle chamber defined therein for receiving material to be vaporized;
    a hot air generator provided in the housing for blowing hot air through said receptacle chamber;
    a valve removably seated on the receptacle;
    a container with at least one opening in communication with the valve for introduction and removal of vapors;
    wherein the receptacle and valve have conical lower ends, and wherein the receptacle is seatable upon the housing, and the valve is seatable upon the receptacle in such a manner that they slide by themselves to their predetermined place as a result of their conical shape and by gravity.

2. An inhaler for providing aroma and/or active substance containing vapors, comprising:
    a housing;
    a receptacle seated on the housing and having a receptacle chamber defined therein for receiving material to be vaporized;
    a hot air generator provided in the housing for blowing hot air through said receptacle chamber;
    a valve removably seated on the receptacle;
    a container with at least one opening in communication with the valve for introduction and removal of vapors;
    wherein the valve further includes a valve cover formed generally funnel-shaped to prevent direct contact between hot air and the container.

3. An inhaler for providing aroma and/or active substance containing vapors, comprising:
    a housing;
    a receptacle seated on the housing and having a receptacle chamber defined therein for receiving material to be vaporized;
    a hot air generator provided in the housing for blowing hot air through said receptacle chamber;
    a valve removably seated on the receptacle;
    a container with at least one opening in communication with the valve for introduction and removal of vapors;
    further comprising a mouthpiece, which is comprised of an outer cylinder which establishes a fixed connection with the valve, as well as an inner cylinder, through the pressure of the lips of an operating person is transmittable to the valve for opening and closing the container opening.

4. An inhaler for providing aroma and/or active substance containing vapors, comprising:
    a housing;
    a receptacle seated on the housing and having a receptacle chamber defined therein for receiving material to be vaporized;
    a hot air generator provided in the housing for blowing hot air through said receptacle chamber;
    a valve removably seated on the receptacle;
    a container with at least one opening in communication with the valve for introduction and removal of vapors;
    wherein the container is a heat-resistant plastic bag.

5. An inhaler according to claim 4, wherein the housing has a shape of a volcano.

6. An inhaler according to claim 4, wherein a crucible is provided, via which a fluid can be vaporized.

7. An inhaler according to claim 4, wherein the receptacle cooperates with the valve such that the valve is seatable and removable from said receptacle.

8. An inhaler according to claim 4, wherein the receptacle further comprises a smoke detector to monitor the vapor for the development of undesired smoke, whereupon the smoke detector provides a signal to a controller to regulate the temperature of the hot air source.

9. An inhaler according to claim 4, wherein said hot air generator blows air heated to 50–300° C. through said receptacle chamber.

10. An inhaler according to claim 4, wherein the housing further includes:
    a temperature regulator to set the temperature in the vaporizing chamber; and
    an on/off switch to control the hot air source.

11. An inhaler for providing aroma and/or active substance containing vapors, comprising:
    a housing;
    a receptacle seated on the housing and having a receptacle chamber defined therein for receiving material to be vaporized;
    a means for blowing hot air through said receptacle chamber, the air heated between 50–300° C.;
    a temperature regulator provided outside the housing for regulating the temperature of the means for blowing hot air;
    an on/off switch for energizing and de-energizing the means for blowing hot air;

a valve removably seated on the receptacle;

an expandable container associated with said valve and with at least one opening in communication with the valve for introduction and removal of vapors.

12. An inhaler for providing aroma and/or active substance containing vapors, comprising:

a housing;

a receptacle seated on the housing and having a receptacle chamber defined therein for receiving material to be vaporized;

a hot air generator provided in the housing for blowing air heated to 50–300° C. through said receptacle chamber, said hot air generator including a heating chamber, an airflow tube connecting the heating chamber to the receptacle, and a motor and propeller for blowing the air through said receptacle;

a temperature regulator provided outside the housing for regulating the temperature of the hot air generator;

an on/off switch for energizing and de-energizing the hot air generator;

a valve removably seated on the receptacle;

an expandable container associated with said valve and with at least one opening in communication with the valve for introduction and removal of vapors.

* * * * *